(12) United States Patent
May et al.

(10) Patent No.: US 7,012,090 B1
(45) Date of Patent: Mar. 14, 2006

(54) PYRANOINDOLES FOR TREATING GLAUCOMA

(75) Inventors: Jesse A. May, Fort Worth, TX (US); Hwang-Hsing Chen, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 355 days.

(21) Appl. No.: 10/220,924

(22) PCT Filed: Nov. 14, 2000

(86) PCT No.: PCT/US00/31142

§ 371 (c)(1),
(2), (4) Date: Sep. 5, 2002

(87) PCT Pub. No.: WO01/70745

PCT Pub. Date: Sep. 27, 2001

Related U.S. Application Data

(60) Provisional application No. 60/190,285, filed on Mar. 17, 2000.

(51) Int. Cl.
*A61K 31/404* (2006.01)
*C07P 491/052* (2006.01)
*A61P 27/06* (2006.01)

(52) U.S. Cl. ..................................... 514/411; 548/430
(58) Field of Classification Search ................ 548/430; 514/411
See application file for complete search history.

(56) References Cited

U.S. PATENT DOCUMENTS

| | | | |
|---|---|---|---|
| 4,436,915 A | 3/1984 | Picart | |
| 4,690,931 A | 9/1987 | Wick et al. | |
| 5,151,444 A | 9/1992 | Ueno et al. | |
| 5,296,504 A | 3/1994 | Stjernschantz et al. | |
| 5,352,708 A | 10/1994 | Woodward et al. | |
| 5,422,368 A | 6/1995 | Stjernschantz et al. | |
| 5,461,061 A | 10/1995 | Wikstrom et al. | |
| 5,494,928 A | 2/1996 | Bös | |
| 5,571,833 A | 11/1996 | Kruse et al. | |
| 5,633,276 A | 5/1997 | North et al. | |
| 5,646,173 A | 7/1997 | Bös | |
| 5,750,556 A | 5/1998 | Mewshaw et al. | |
| 5,874,477 A | 2/1999 | McConnell et al. | |
| 5,889,052 A | 3/1999 | Klimko et al. | |
| 5,902,815 A | 5/1999 | Olney et al. | |

FOREIGN PATENT DOCUMENTS

| | | |
|---|---|---|
| EP | 0 708 099 B1 | 11/2001 |
| WO | WO 94/13275 A1 | 6/1994 |
| WO | WO 98/31354 A3 | 7/1998 |
| WO | WO 98/31354 A2 | 7/1998 |
| WO | WO 00/12475 A1 | 3/2000 |
| WO | WO 00/16761 A3 | 3/2000 |
| WO | WO 00/16761 A2 | 3/2000 |
| WO | WO 00/35922 A1 | 6/2000 |

OTHER PUBLICATIONS

Macor et al. publication, Journal of Medicinal Chemistry, 1992, 35:3625–3632.*
Beresford, Isabel et al., "GR196429: A Nonindolic Agonist at High–Affinity Melatonin 1 Receptors", J. Pharmacol. Exp. Ther. 285:1239–1245 (1998).
Bös et al., "Novel Agonists of 5HT2C Receptors. Synthesis and Biological Evaluation of Substituted 2–(Indol–1–yl)–1–methylethylamines and 2–(Indeno[1,2–b]pyrrol–1–yl)–1–methylethylamines. Improved Therapeutics for Obsessive Compulsive Disorder", J. Med. Chem., vol. 40, pp 2762–2769 (1997).
Bowen et al., "Nonlinear regression using spreadsheets", Trends in Pharmacological Sciences, 16:413 (1995.
Carvalho, C. E. and Sargent, M. V., "Naturally Occurring Dibenzofurans, Part 5.1 Synthesis of Melacarpic Acid", J. Chem. Soc., Perkin 1:1613–1620 (1984).
Dostert, Philippe. et al., "Interactions of Monoamine Oxidase with Substrates and Inhibitors", Medicinal Res. Rev., 9:45–89 (1989).
Fiorella, et al., "Role of 5–HT2A and 5–HT2C receptors in the stimulus effects of hallucinogenic drugs II: reassessment of LSD false positives", Psychopharmacology, 121:357 (1995).
Flaugh, M. E., et al., "Synthesis and Evaluation of the Antiovulatory Activity of a Variety of Melatonin Analogues", Journal of Medicinal Chemistry, 22:63–69 (1979).
Glennon et al., "Binding Of Benz[e]– And Benz[g]–Fused Tryptamine Derivatives At Serotonin Receptors: Evidence For A Region Of Bulk Tolerance", Medicinal Chemistry Research, vol. 1, pp 201–206 (1991).
Glennon, R. A., et al., "Binding of Indolylalkylamines at 5–HT2 Serotonin Receptors: Examination of a Hydrophobic Binding Region", J. Med. Chem., 33:2777–2784 (1990).
Griffin, B. W., et al., "Pharmacological Characterization of an FP Prostaglandin Receptor on Rat Vascular Smooth Muscle Cells (17r5) Coupled to Phospholnositide Turnover and Intracellular Calcium Mobilization", J. Pharmacol. Exp. Ther., 286:411–418 (1998).
Johnson, et al., "Binding To The Serotonin 5–HT2 Receptor By The Enantiomers of 125I–DOI", Neuropharmacology, vol. 26, No. 12, 1803–0806 (1987).
Macor, J. E., et al. "The Synthesis of Conformationally/ Rotationally Restricted Analogs of the Neurotransmitter Serotonin", Tetrahedron Lett. 35:45–48 (1994).
Macor, J. E., et al., "The Synthesis of Pyrano[3,2–e]indoles and Pyranol[2,3–f]indoles as Rotationally Restricted Phenolic Analogs of the Neurotransmitter Serotonin", Tetrahedron, 48:1039–1052 (1992).

(Continued)

Primary Examiner—Rita Desai
Assistant Examiner—Robert Shiao
(74) Attorney, Agent, or Firm—Barry L. Copeland; Teresa J. Schultz

(57) ABSTRACT

Substituted pyranoindoles useful for lowering and controlling IOP and glaucoma are disclosed.

11 Claims, No Drawings

OTHER PUBLICATIONS

Macor, John E., et al., "1-(2-Aminoethyl)-3-methyl-8,9-dihydropyrano[3,2-?]indole: A Rotationally Restricted Phenolic Analog of the Neurotransmitter Serotonin and Agonist Selective for Serotonin (5–HT2–Type) Receptors", Journal Of Medicinal Chemistry, vol. 35, No. 20. pp. 3625–3632 (1992).

Parkinson, Andrews, "Biotransformation Of Xenobiotics", Casaret & Doull's Toxicology, 5th Ed., C.D. Klassan Ed., 129–130 144–146 (1996).

Somel, M. et al., "Syntheses of (±)–Claviciptic Acid And Its Derivatives", Heterocycles 37:719–724 (1994).

* cited by examiner

PYRANOINDOLES FOR TREATING GLAUCOMA

This application claims priority from PCT/US00/31142 filed on Nov. 14, 2000, and U.S. Ser. No. 60/190,285, filed on Mar. 17, 2000.

The present invention is directed to novel substituted pyranoindoles. These novel compounds are useful for lowering and controlling normal or elevated intraocular pressure (IOP) and treating glaucoma.

BACKGROUND OF THE INVENTION

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be a high risk for the eventual development of the visual loss associated with glaucoma Some patients with glaucomatous field loss have relatively low intraocular pressure. These so called normo-tension or low tension glaucoma patients can also benefit from agents that lower and control IOP. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

It has been found that serotonergic compounds which possess agonist activity at $5\text{-}HT_2$ receptors effectively lower and control normal and elevated IOP and are useful for treating glaucoma, see commonly owned co-pending application, PCT/US99/19888. Compounds that act as agonists at $5\text{-}HT_2$ receptors are well known and have shown a variety of utilities, primarily for disorders or conditions associated with the central nervous system (CNS). U.S. Pat. No. 5,494,928 discloses certain 2-(indol-1-yl)-ethylamine derivatives that are $5\text{-}HT_{2C}$ agonists for the treatment of obsessive compulsive disorder and other CNS derived personality disorders. U.S. Pat. No. 5,571,833 discloses tryptamine derivatives that are 5-HT2 agonists for the treatment of portal hypertension and migraine. U.S. Pat. No. 5,874,477 discloses a method for treating malaria using $5\text{-}HT_{2A/2C}$ agonists. U.S. Pat. No. 5,902,815 discloses the use of $5\text{-}HT_{2A}$ agonists to prevent adverse effects of NMDA receptor hypo-function. WO98/31354A2 discloses $5\text{-}HT_{2B}$ agonists for the treatment of depression and other CNS conditions. WO00/12475 discloses indoline derivatives as $5\text{-}HT_{2B}$ and $5\text{-}HT_{2C}$ receptor agonists for the treatment of a variety of disorders of the central nervous system, but especially for the treatment of obesity. WO00/35922 discloses certain pyrazino[1 2-a]quinoxaline derivatives as $5\text{-}HT_{2C}$ agonists for the treatment of obsessive-compulsive disorder, depression, eating disorders, and other disorders involving the CNS. Agonist response at the $5\text{-}HT_{2A}$ receptor is reported to be the primary activity responsible for hallucinogenic activity, with some lesser involvement of the $5\text{-}HT_{2C}$ receptor possible [Psychopharmacology, Vol. 121:357, 1995].

Certain pyrano[3,2-e]indol-3-ethylamines and the corresponding N,N-dimethylamino analogs have been reported in conjunction with serotonin receptor binding profile studies [*J. Med. Chem.* 35, 3625 (1992)]. These compounds have been shown to possess good affinity at the serotonin $5\text{-}HT_2$ receptor, though no utility has been associated with these compounds. The synthesis of other pyrano[3,2-e]indoles bearing a tertiary amine, either 3-[(N-methylpyrrolidin-2-yl)methyl] or 3-(N-methylpyrrolidin-3-yl), has been reported [*Tetrahedron Lett.* 35, 45 (1994)], but no utility was noted for these compounds. The rapid metabolic deamination of primary arylethylamines in general, and tryptamines in particular, by monoamine oxidase [*Principles of Drug Action*, $3^{rd}$ Ed., p382 (1990)] is a significant impediment to the use of such compounds as therapeutic agents. It has been noted that this rapid oxidative deamination can be dramatically retarded or eliminated by the incorporation of an alkyl group on the carbon atom in the position alpha to the primary amine [Biotransformation of Xenobiotics, in *Casaret & Doull's Toxicology*, 5th ed., C. D. Klaassen Ed., pp. 129–145 (1996); *Medicinal Res. Rev.* 9, 45 (1989)]. Therefore, compounds bearing such an alpha alkyl group, such as those of the present disclosure, would be anticipated to provide a distinct therapeutic advantage.

Application EP 708,099 (1996) is concerned with the utility of selected pyrano[3,2-e]indoles as melatonin receptor agonists; and is, therefore, directed exclusively toward 3-(N-acyl-aminoalkyl)pyrano[3,2-e]indoles, that is non-basic amide derivatives, compounds that do not incorporate a basic primary amine, a functionality critical to the compounds of the present disclosure. U.S. Pat. No. 5,461,061 discloses certain unexampled 8-amino-pyrano[3,2-e]indol-1-alkylamines that are noted as selective $5\text{-}HT_{1A}$ agonists useful for treating CNS disorders including depression, anxiety, senile dementia and obsessive compulsive disturbances. The indoline derivatives of U.S. Pat. No. 5,633,276 (1997), that is 1-(N-acyl-aminoethyl) furano- and pyrano[2,3-g]indole derivatives, are also non-basic compounds which are melatonin receptor modulators, most preferably agonists [*J. Pharmacol. Exp. Ther.* 285, 1239 (1998)], that are useful for the treatment of conditions associated with a disturbed melatonin system.

SUMMARY OF THE INVENTION

The present invention is directed to new derivatives of pyrano[3,2-e]indol-3-ethylamine and pyrano[2,3-g]indol-1-ethylamine which can be used to lower and control IOP associated with normal-tension glaucoma, ocular hypertension, and glaucoma in warm blooded animals, including man. The compounds are formulated in pharmaceutical compositions suitable for topical delivery to the eye.

DESCRIPTION OF THE PREFERRED EMBODIMENTS

Compounds that are useful according to the present invention are represented by the following Formula I.

FORMULA I

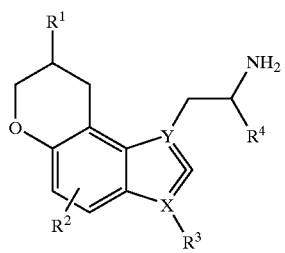

Wherein $R^1$ is chosen from hydrogen, halogen, hydroxyl, $C_{1-6}$alkyl, $C_{1-6}$alkoxy, $NR^5R^6$;

$R^2$ is chosen from hydrogen, halogen or $C_{1-6}$alkyl;

$R^3$ and $R^5$ are chosen from hydrogen or $C_{1-6}$alkyl;

$R^4$ is $C_{1-4}$alkyl;

$R^6$ is chosen from hydrogen, $C_{1-6}$alkyl or $C(=O)C_{1-4}$alkyl;

X and Y are nitrogen or carbon, but X and Y cannot be the same;

the dashed bonds ( - - - ) denote a suitably appointed double bond and single bond;

when Y is nitrogen the dashed bonds can both be single bonds;

and pharmaceutically acceptable salts and solvates of the compounds.

It is recognized that compounds of Formula I can contain one or more chiral centers. This invention contemplates all enantiomers, diastereomers and, mixtures thereof.

In the above definitions, the total number of carbon atoms in a substituent group is indicated by the $C_{i-j}$ prefix where the numbers i and j define the number of carbon atoms; this definition includes straight chain, branched chain, and cyclic alkyl or (cyclic alkyl)alkyl groups.

It is important to recognize that a substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

Synthesis

The desired substituted 1-(α-alkyl-ethylamino)-3,7,8,9-tetrahydro-pyrano[3,2-e]indoles 4 of Formula I can be prepared from the appropriately substituted 3,7,8,9-tetrahydro-pyrano[3,2-e]indoles 1 by the well known sequence (Scheme 1) involving Vilsmeier-Haack formylation of the indole compound, e.g. 1, followed by condensation of the resulting carboxaldehyde (2) with the appropriate nitroalkane to give the corresponding nitroalkene (3), which is subsequently reduced with, e.g. LiAlH₄, to give the desired compounds 4 of Formula I [*Heterocycles* 37, 719 (1994), *J. Med. Chem.* 35, 3625 (1992), *J. Med. Chem.* 33, 2777 (1990), *J Chem. Soc.*, 3493 (1958)].

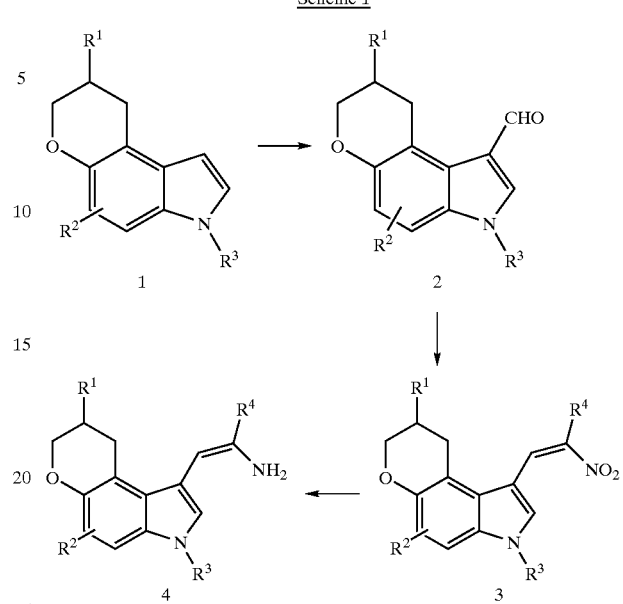

The 3,7,8,9-tetrahydro-pyrano[3,2-e]indoles 1 can be prepared from the appropriate 5- or 6-substituted 3-methyl-4-nitro-phenols [e.g. Synth. Commun. 16, 63 (1986), J. Chem. Soc., Perkin 1, 1613 (1984), *J. Med. Chem.* 22, 63 (1979)] via the 7- or 8-substituted 5-methyl-6-nitro-chroman intermediate according to the procedure described in Tetrahedron 48, 1039 (1992). Desired 8-substituted indoles 1 can be prepared from the appropriate phenols as outlined in Scheme 2. Furthermore, functional group transformations well known in the art can be used to transform the hydroxyl group to other functional groups, for example, a halogen substituent or an amino or alkylamino group.

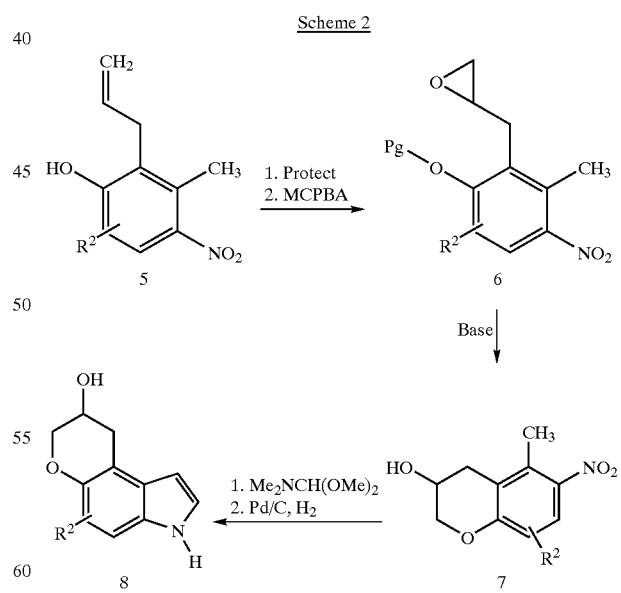

The desired pyrano[2,3-g]indol-1-(α-alkyl-ethilamines) 12 of Formula I can be prepared from the appropriately substituted 1,7,8,9-tetrahydro-pyrano[2,3-g]indole 9 by methods well known in the art and described in Scheme 3 [U.S. Pat. No. 5,494,928 (1997); J. Med. Chem., 40, 2762, (1997)].

Scheme 3

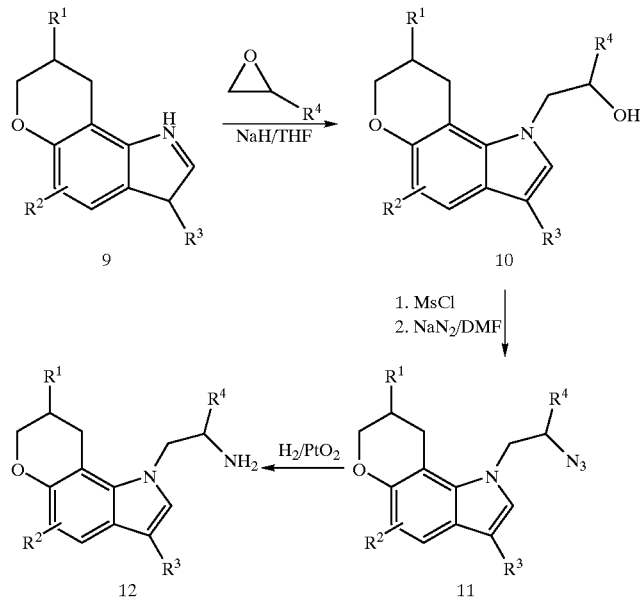

Alternately, the compounds 12 can be prepared by the method of Scheme 4. Reaction of 9 with the activated alaninol 13, wherein the hydroxyl group has been suitably activated toward subsequent nucleophilic amination by formation of a sulfonate ester [J. Chem. Soc., Perkin 1, 1479, (1981)], e.g. methansulfonyl, toluenesulfonyl, bromophenylsulfonyl, or nitrophenylsulfonyl, provides 14 which following N-deprotection gives compounds 12 of Formula I.

Scheme 4

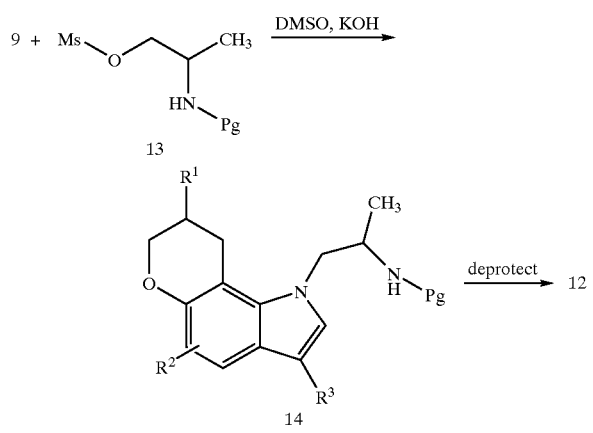

The 1,7,8,9-tetrahydro-pyrano[2,3-g]indole intermediates 9 can be prepared from the appropriate 6-formyl-chromane by the method described in Can. J. Chem. 60, 2093 (1982) or from the appropriate 5-amino-chromane by the method described in U.S. Pat. No. 5,633,276 (1997).

The compounds of this invention, Formula I, can be incorporated into various types of ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, surfactants, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as, hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8. The compounds will normally be contained in these foundations in an amount 0.01% to 5% by weight, but preferably in an amount of 0.25% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., briazolamide and dorzolamide), $\alpha_1$ antagonists (e.g. nipradolol), $\alpha_2$ agonists (e.g., iopidine and brimonidine), miotics (e.g., pilocarpine and epinephrine), prostaglandin analogs (e.g., latanoprost, travaprost, unoprostone, and compounds set forth in U.S. Pat. Nos. 5,889,052; 5,296,504; 5,422,368; and 5,151,444, "hypotensive lipids" (e.g., lumigan and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 06/203350, and appropriate compounds from WO94/13275, including memantine.

The following examples are given to illustrate the preparation of compounds that are the subject of this invention but should not be construed as implying any limitations to the claims. The preferred compounds of Formula I are described in Examples 1, 3, 4, and 6. The most preferred is the compound of Example 4. The proton magnetic resonance spectrum of each compound of the Examples was consistent with the assigned structure.

Method 1

5HT$_2$ Receptor Binding Assay

In order to determine the relative affinities of serotonergic compounds at the 5-HT$_2$ receptors, their ability to compete for the binding of the agonist radioligand [$^{125}$I]DOI to brain 5-HT2 receptors is determined as described below with minor modification of the literature procedure [Neuropharmacology, 26, 1803 (1987)]. Aliquots of post mortem rat or human cerebral cortex homogenates (400 µl) dispersed in 50 mM TrisHCl buffer (pH 7.4) are incubated with [$^{125}$I]DOI (80 pM final) in the absence or presence of methiothepin (10 µM final) to define total and non-specific binding, respectively, in a total volume of 0.5 ml. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter. The concentration of the compound needed to inhibit the [$^{125}$I]DOI binding by 50% of the maximum is termed the IC$_{50}$ value. A compound is considered to possess high affinity for the 5-HT$_2$ receptor if the IC$_{50}$ value is less than 50 nM.

Method 2

5-HT$_2$ Functional Assay: Phosphoinositide (PI) Turnover Assay

The relative agonist activity of serotonergic compounds at the 5-HT$_2$ receptor can be determined in vitro using the ability of the compounds to stimulate the production of [$^3$H]inositol phosphates in [$^3$H]myo-inositol-labeled A7r5 rat vascular smooth muscle cells by their ability to activate the enzyme phospholipase C. These cells are grown in culture plates, maintained in a humidified atmosphere of 5% CO$_2$ and 95% air and fed semi-weekly with Dulbecco's modified Eagle medium (DMEM) containing 4.5 g/l glucose and supplemented with 2 mM glutamine, 10 µg/ml gentamicin, and 10% fetal bovine serum. For the purpose of conducting the phosphoinositide (PI) turnover experiments, the A7r5 cells are cultured in 24-well plates as previously [J. Pharmacol. Expt. Ther., 286, 411 (1998)]. Confluent cells are exposed for 24–30 hrs to 1.5 µCi [$^3$H]-myo-inositol (18.3 Ci/mmol) in 0.5 ml of serum-free medium. Cells are then rinsed once with DMEM/F-12 containing 10 mM LiCl prior to incubation with the test agent (or solvent as the control) in 1.0 ml of the same medium for 1 hr at 37° C., after which the medium is aspirated and 1 ml of cold 0.1 M formic acid added to stop the reaction. The chromatographic separation of [$^3$H]-inositol phosphates ([$^3$H]-IPs) on an AG-1-X8 column is performed as previously described [J. Pharmacol. Expt. Ther. 286, 411 (1998)] with sequential washes with H$_2$O and 50 mM ammonium formate, followed by elution of the total [$^3$H]-IPs fraction with 1.2 M ammonium formate containing 0.1 M formic acid. The eluate (4 ml) is collected, mixed with 15 ml scintillation fluid, and the total [$^3$H]-IPs determined by scintillation counting on a beta-counter. Concentration-response data are analyzed by the sigmoidal fit function of the Origin Scientific Graphics software (Microcal Software, Northampton, Mass.) to determine agonist potency (EC$_{50}$ value) and efficacy (E$_{max}$). Serotonin (5-HT) is used as a positive control (standard) agonist compound and the efficacy of test compounds is compared to that of 5-HT (set at 100%). The concentration of the compound needed to stimulate the production of [$^3$H]-IPs by 50% of the maximum response is termed the EC$_{50}$ value. Compounds are considered potent agonists if their EC$_{50}$ values in this functional assay are ≦1 µM and are considered full agonists if their efficacy is >80% of that of 5-HT.

The above procedures were used to generate the data shown in Table 1.

TABLE 1

5-HT$_2$ Receptor Binding and Functional Data.

| Compound | IC$_{50}$, nM | EC$_{50}$, nM | Efficacy (E$_{max}$, %) |
|---|---|---|---|
| (R)-DOI | 0.46 | 27.7 | 82 |
| Example 1 | 0.82 | 189 | 119 |
| Example 3 | 0.72 | 116 | 81 |
| Example 4 | — | 111 | 109 |
| Example 6 | 1.95 | 300 | 92 |

Method 3

Acute IOP Response in Lasered (Hypertensive) Eyes of Conscious Cynomolgus Monkeys Intraocular pressure (IOP) was determined with an Alcon Pneumatonometer after light corneal anesthesia with 0.1% proparacaine. Eyes were washed with saline after each measurement. After a baseline IOP measurement, test compound was instilled in one 30 µL aliquot to the right eyes only of nine cynomolgus monkeys. Vehicle was instilled in the right eyes of six additional animals. Subsequent IOP measurements were taken at 1, 3, and 6 hours. A compound is considered efficacious in this model of ocular hypertension if there is a decrease in the baseline IOP of the lasered eye (O.D.) of at least 20% following topical administration.

The profile of the IOP response following topical administration of representative compounds is provided in Table 2.

TABLE 2

IOP Response in Conscious Cynomolgus Monkeys

| Compound | Dose, µg | Baseline IOP (mmHg) | Percent IOP Reduction ± SEM Hours after Dose | | |
|---|---|---|---|---|---|
| | | | 1 | 3 | 6 |
| (R)-DOI | 100 | 31.9 | 11.0 ± 4.98 | 25.3 ± 2.97 | 34.4 ± 4.98 |
| Example 1 | 300 | 41.9 | 18.8 ± 3.31 | 28.0 ± 5.20 | 26.1 ± 5.35 |
| Example 3 | 300 | 36.7 | 16.0 ± 3.79 | 28.0 ± 5.49 | 22.9 ± 6.70 |

EXAMPLE 1

1-Methyl-2-(3-methyl3,7,8,9-tetrabydro-pyrano[3,2-e]indol-1-yl)-ethylamine hydrochloride

Step A. 1-(2-Nitropropenyl)-3-methyl-3,7,8,9-tetrahydro-pyrano[3,2-e]indole

A mixture of 3-methyl-3,7,8,9-tetrahydro-pyrano[3,2-e]indole-1-carboxaldehyde (1.02 g, 4.74 mmol) and ammonium acetate (0.30 g, 3.90 mmol) in 12 ml of nitroethane was heated at 100° C. for 3 h, stirred at room temperature for 18 h, mixed with water (50 ml) and extracted with EtOAc (3×50 ml). The combined extracts were dried ($MgSO_4$), filtered and evaporated to dryness. Crystallization of the residue from a mixture of dichloromethane and hexane gave an orange solid (1.10 g, 85%): mp 200–202° C.

Step B. 1-Methyl-2-(3-methyl-3,7,8,9-tetrahydro-pyrano[3,2-e]indol-1yl)-ethylamine hydrochloride To a stirred solution of the product from Step A (0.90 g, 3.31 mmol) in anhydrous THF (50 ml) under nitrogen was added a 1 M solution of lithium aluminum hydride in THF (17.0 ml, 17 mmol). The resulting mixture was heated at 50° C. for 2 h, cooled to room temperature and the reaction was quenched by the addition of water (0.68 ml), 15% NaOH (0.68 ml) and water (2.0 ml). The suspension was stirred for 2 h, filtered and washed with THF (50 ml). The filtrate was concentrated, mixed with 2 N HCl (200 ml) and extracted with EtOAc (2×50 ml) to remove the starting material. The pH of the aqueous was adjusted to above 12 with 50% NaOH, and this solution was extracted with EtOAc (3×80 ml). The combined extracts were dried ($MgSO_4$), filtered and evaporated to dryness. The crude oil was dissolved in a mixture of ethyl acetate and ethanol and treated with 1 N solution of HCl in ether. The solid that formed was collected by filtration and dried (65° C., vacuum) to afford an off-white solid (0.297 g, 32%); mp 214–217° C. Analysis. Calcd. for $C_{15}H_{20}N_2O.HCl.0.25\ H_2O$: C, 63.14; H, 7.59; N, 9.82. Found: C, 63.18; H, 7.46; N, 9.65.

EXAMPLE 2

1-Methyl-2-(3,7,8,9-tetrahydro-pyrano[3,2-e]indol-1-yl)-ethylamine maleate

Step A. 1-(2-Nitropropenyl)3,7,8,9-tetrahydro-pyrano[3,2-e]indole

A mixture of 3,7,8,9-tetrahydro-pyrano[3,2-e]indole-1-carboxaldehyde (0.90 g, 4.48 mmol) and ammonium acetate (0.34 g, 4.48 mmol) was treated as described for Example 1, Step A to give, after crystallization, an orange solid (0.95 g, 82%). mp 246–247° C.

Step B. 1-Methyl-2-(3,7,8,9-tetrahydro-pyrano[3,2-e]indol-1-yl)-ethylamine maleate The product from Step A was treated as described for Example 1, Step B, but isolated as the maleic acid salt to give an off-white solid (9%). Analysis. Calcd. for $C_{14}H_{18}N_2O.C_4H_4O_4.0.25\ H_2O$: C, 61.61; H, 6.46; N, 7.98. Found: C, 61.66; H, 6.34; N, 7.91.

EXAMPLE 3

1-Methyl-2-(3,7,8,9-tetrahydro-pyrano[3,2-e]indol-1-yl)-ethylamine hydrochloride

The product from Example 2, Step A (1.45 g, 5.62 mmol) in anhydrous THF (50 ml) was treated as described for Example 1, Step B, but the crude oil was purified by chromatography (silica, dichloromethane/methanol/triethylamine, 10:1:0.5) to give a solid which was dissolved in ethanol and treated with a 1 N solution of HCl in ether. Recrystallization from a mixture of ethanol and ethyl acetate gave a beige solid (0.65 g, 40%): mp 270–271° C. Analysis. Calcd. for $C_{14}H_{18}N_2O.HCl.0.33\ C_2H_5OH.0.33\ H_2O$: C, 61.31; H, 7.54; N, 9.79. Found: C, 61.37; H, 7.54; N, 9.65.

EXAMPLE 4

(R)-1-Methyl-2-(3,7,8,9-tetrahydro-pyrano[3,2-e]indol-1-yl)ethylamine hydrochloride

Step A. (S)-1-(2-Hydroxypropyl)3,7,8,9-letrahydro-pyrano[3,2-e]indole

To a solution of 3,7,8,9-tetrahydro-pyrano[3,2-e]indole (1.00 g, 5.78 mmol) in anhydrous THF (50 ml) at 0° C. was added a solution of ethylmagnesium bromide (1.0 M in tert-butyl methyl ether, 6.94 ml, 6.94 mmol). The mixture was stirred for 10 min and (S)-propylene oxide (0.50 g, 8.67 mmol) was added. This mixture was stirred for 15 h and then poured into a saturated solution of ammonium chloride, which was extracted with EtOAc (2×100 ml). The combined extracts were dried (MgSO4) and evaporated to a residue that was purified by column chromatography (silica, 20 to 40 EtOAc in hexane) to give an oil (0.36 g, 27%).

Step B. (R)-1-(2-Azidopropyl)-3,7,8,9-tetrahydro-pyrano[3,2-e]indole

Methanesulfonic anhydride (0.477 g, 2.73 mmol) was added to a solution of the product from Step A (0.35 g, 1.52 mmol) and triethylamine (0.46 g, 4.55 mmol) in anhydrous THF (50 ml) at 0° C. The mixture was stirred for 30 min and sodium azide (0.59 g, 9.1 mmol) was added followed by evaporation to a residue; anhydrous DMF (50 ml) was added and the mixture heated at 90° C. for 1 h. The reaction mixture was poured into ice water (100 ml) and this mixture was extracted with EtOAc (2×75 ml). The combined extracts were dried ($MgSO_4$) and evaporated to a residue that was purified by column chromatography (silica, 10 to 20% EtOAc in hexane) to give an oil (0.26 g, 67%): LCMS (APCI) 257 (M+H).

Step C. (R)-1-Methyl-2-(3,7,8,9-tetrahydropyrano[3,2-e]indol-1-yl)-ethylamine hydrochloride A mixture of the product from Step B (0.26 g, 1.01 mmol) and 10% Pd/C (0.026 g) was stirred under hydrogen for 5 h filtered and evaporated to dryness. The residue was dissolved in EtOAc, 1 N HCl/EtOH was added, and the mixture was evaporated to a solid. Crystallization from MeOHl-EtOAc gave a yellowish solid (0.221 g, 79%): mp 262–264° C.; $[\alpha]_D^{25}$+24.8° (c=0.206, MeOH). Analysis. Calcd. for $C_{15}H_{20}N_2O.HCl.0.5\ H_2O$: H, 7.31; C, 60.95; N, 10.15. Found: H, 7.49; C, 61.25; N, 9.75.

EXAMPLE 5

(S)-1-Methyl-2-(3,7,8,9-tetrahydro-pyrano[3,2-e]indol-1-yl)-ethylamine hydrochloride

This compound was prepared by following the same procedure described in Example 4, but using R-propylene oxide in Step A: 49% yield; mp 261–263° C.; $[\alpha]_D^{25}$−25.6° (c=0.29, MeOH). Analysis. Calcd. for $C_{15}H_{20}N_2O.HCl.0.5\ H_2O.0.1\ CH_3OH$: C, 60.68; H, 7.37; N, 10.04. Found: C, 60.90; H, 7.48; N, 9.67.

EXAMPLE 6

1-(2-Aminopropyl)-3,7,8,9-tetrahydro-pyrano[3,2-e]indol-8-ol hydrochloride

Step A: Acetic acid 3-methyl-4-nitro-2-(2-propenyl)-phenyl ester

To a solution of 3-methyl-4-nitro-2-(2-propenyl)-phenol (5.19 g, 26.9 mmol) in dichloromethane (200 ml) at 0° was added triethylamine (5.43 g, 53.8 mmol) and acetic anhydride (3.29 g, 32.3 mmol). After 30 min, the reaction mixture was evaporated to a residue which was purified by chromatography (silica, 2% to 10% ethyl acetate in hexane) to give an orange oil (4.80 g, 76%).

Step B: 5-Methyl-6-nitro-chroman-3-ol

To a solution of the product from Step A (1.89 g, 8.04 mmol) in dichloromethane (150 ml) was added MCPBA (2.53 g, 14.63 mmol). The mixture was stirred overnight at ambient temperature, extracted with EtOAc (2×200 ml) and washed with a saturated solution of sodium bicarbonate. The combined extracts were dried, filtered and evaporated to give a residue which was purified by chromatography (silica, 10% to 20% ethyl acetate in hexane) to give the epoxide as an oil (1.46 g, 72%). A solution of the epoxide (1.44 g, 5.74 mmol) in THF (30 ml) was combined with a 2 N NaOH solution (6 ml, 12 mmol). Methanol (10 ml) was added to provide a solution, which was stirred for 4 h. The reaction mixture was evaporated to a residue, which was dissolved in EtOAc and washed with water. The EtOAc was dried and evaporated to give an oil (1.12 g, 93%).

Step C: 3,7,8,9-Tetrahydro-pyrano[3,2-e]indol-8-ol

A mixture of the product from Step B (2.35 g, 11.2 mmol) and dimethylforamide dimethyl acetal (5 ml) in DMF (10 ml) was heated at 164° C. for 64 h under nitrogen and then evaporated to dryness. The residue was dissolved in EtOH (100 ml) and 10% palladium-on-carbon (0.20 g) was added. The mixture was stirred under an atmosphere of hydrogen for 2 days, filtered and evaporated to dryness. The residue was combined with a mixture of EtOAc in dichloromethane and silica and filtered. Purification by chromatography (silica, 25% to 35% ethyl acetate in hexane) gave an oil (0.77 g, 36%).

Step D: 8-Hydroxy-3,7,8,9-tetrahydro-pyrano[3,2-e]indole-1-carboxaldehyde

To a mixture of DMF (2.0 ml) and POCl$_3$ (0.687 g, 4.48 mmol) under nitrogen was added a solution of the product from Step C (0.77 g, 4.07 mmol) in DMF (1.2 ml). The mixture was heated at 40° C. for 1.5 h, cooled, and ice (10 g) was added to the mixture followed by 2 N NaOH. This mixture was heated at 70° C. for 1 h, cooled to ambient temperature, and extracted with EtOAc (3×100 ml). The combined extracts were dried and evaporated to a residue, which was purified by chromatography (silica, 50% to 90% ethyl acetate in hexane) to give a solid (0.67 g, 76%): mp 158–162° C.; MS (ES–) 216 (M–H).

Step E: 1-(2-Nitropropenyl)-3,7,8,9-tetrahydro-pyrano[3,2-e]indol-8-ol

A mixture of the product from Step D (0.64 g, 2.95 mmol) and ammonium acetate (0.23 g, 2.98 mmol) in nitroethane (3 ml) was heated at 115° C. for 2.5 h. The mixture was cooled and the orange solid that formed was collected by filtration, washed with EtOAc and water and dried under vacuum (0.54 g, 67%): mp 240–242° C.

Step F: 1-(2Amninopropyl)-3,7,8,9-tetrahydro-pyrano[3,2-e]indol-8-ol hydrochloride To a mixture of the product from Step E (0.54 g, 1.98 mmol) in THF (50 ml) was added LiAlH$_4$ (1 M, 5.93 ml) and the mixture was heated at 70° C. for 3 h. The reaction mixture was cooled and water and 15% NaOH were added. After stirring for 1 h at ambient temperature the precipitate was removed by filtration; the filtrate was concentrated, mixed with EtOAc, and washed with brine. The crude product was purified by RP-HPLC (C-18 column, 0% to 60% acetonitrile in water containing 0.1% TFA) to give a viscous oil. The oil was converted to the hydrochloride salt (0.20 g, 36%): mp 187–192° C.; MS(ES+) 247 (M+H).

The following topical ophthalmic formulations are useful according to the present invention administered 1–4 times per day according to the discretion of a skilled clinician.

EXAMPLE 7

| Ingredients | Amount (wt %) |
| --- | --- |
| Compound of Example 3 | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 8

| Ingredients | Amount (wt %) |
| --- | --- |
| Compound of Example 1 | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 9

| Ingredients | Amount (wt %) |
| --- | --- |
| Compound of Example 3 | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 10

| Ingredients | Amount (wt %) |
| --- | --- |
| Compound of Example 1 | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |

We claim:
1. A compound of the formula:

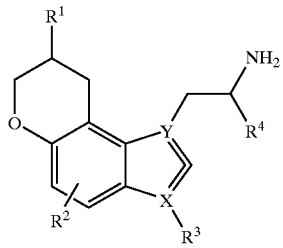

wherein $R^1$ is chosen from halogen, hydroxyl, $C_{1-6}$alkyl, $C_{1-6}$alkoxy, $NR^5R^6$; $R^2$ is chosen from hydrogen, halogen or $C_{1-6}$alkyl; $R^3$ and $R^5$ are chosen from hydrogen or $C_{1-6}$alkyl; $R^4$ is $C_{1-4}$alkyl; $R^6$ is chosen from hydrogen, $C_{1-6}$alkyl or $C(=O)C_{1-4}$alkyl;

X and Y are nitrogen or carbon, but X and Y cannot be the same; the dashed bonds ( - - - ) denote a suitably appointed double bond and single bond; when Y is nitrogen the dashed bonds can both be single bonds; with a proviso when X is nitrogen, Y is carbon, the dashed bonds ( - - - ) denote a double bond between Y and its adjacent carbon and denote a single bond between X and its adjacent carbon, and $R^3$ and $R^4$ independently are $C_{1-4}$ alkyl, wherein $R^3$ and $R^4$ independently are methyl, and pharmaceutically acceptable salts and solvates of the compounds.

2. The compound of claim 1 which is:
1-(2-aminopropyl)-3,7,8,9,-tetrahydro-pyrano-[3,2-e]indol-8-ol.

3. A composition for lowering and controlling normal or elevated intraocular pressure and treating glaucoma, comprising a compound of the formula:

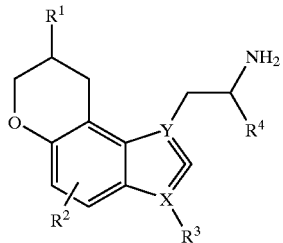

wherein $R^1$ is chosen from halogen, hydroxyl, $C_{1-6}$alkyl, $C_{1-6}$alkoxy, $NR^5R^6$;

$R^2$ is chosen from hydrogen, halogen or $C_{1-6}$alkyl; $R^3$ and $R^5$ an chosen from hydrogen or $C_{1-6}$alkyl; $R^4$ is $C_{1-4}$alkyl; $R^6$ is chosen from hydrogen, $C_{1-6}$alkyl or $C(=O)C_{1-4}$alkyl;

X and Y are nitrogen or carbon, but X and Y cannot be the same; the dashed bonds ( - - - ) denote a suitably appointed double bond and a single bond; when Y is nitrogen the dashed bonds can both be single bonds; with a proviso when X is nitrogen, Y is carbon, the dashed bonds ( - - - ) denote a double bond between Y and its adjacent carbon and denote a single bond between X and its adjacent carbon, and $R^3$ and $R^4$ independently are $C_{1-4}$ alkyl, wherein $R^3$ and $R^4$ independently are methyl, and pharmaceutically acceptable salts and solvates of the compounds.

4. The composition of claim 3 wherein the compound is:
1-(2-aminopropyl)3,7,8,9-tetrahydro-pyrano[3,2-e]indol-8-ol.

5. A method for lowering and controlling normal or elevated intraocular pressure and treating glaucoma, which comprises administering a pharmaceutically effective amount of a compound of the formula:

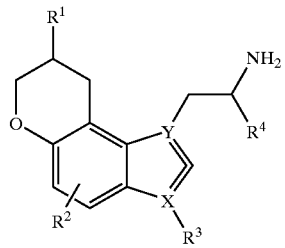

wherein $R^1$ is chosen from hydrogen, halogen, hydroxyl, $C_{1-6}$alkyl, $C_{1-6}$alkoxy, $NR^5R^6$;

$R^2$ is chosen from hydrogen, halogen or $C^{1-6}$alkyl; $R^3$ and $R^5$ are chosen from hydrogen or $C_{1-6}$alkyl; $R^4$ is $C_{1-4}$alkyl; $R^6$ is chosen from hydrogen, $C_{1-6}$alkyl or $C(=O)C_{1-4}$alkyl;

X and Y are nitrogen or carbon, but X and Y cannot be the same; the dashed bonds ( - - - ) denote a suitably appointed double bond and single bond; when Y is nitrogen th dashed bonds can both be single bonds; and pharmaceutically acceptable salts and solvates of the compounds.

6. The method of claim 5 wherein the compound is selected from the group consisting of:
1-methyl-2-(3-methyl-7,8,9-tetrahydro-pyrano[3,2-e]indol-1-yl)-ethylamine;
1-methyl-2-(3,7,8,9-tetrahydro-pyrano[3,2-e]indol-1yl)-ethylamine;
(R)-1-methyl-2-(3,7,8,9-tetrahydro-pyrano[3,2-e]indol-1-yl)-ethylamine; and
1-(2aminopropyl)3,7,8,9-tetrahydro-pyrano[3,2-e]indol-8-ol.

7. The method of claim 6 wherein the compound is 1-methyl-2(3,7,8,9-tetrahydro-pyrano[3,2-e]indol-1-yl)-ethylamine.

8. The method of claim 5, further comprising administering one or more other agent for treating glaucoma, wherein said agent is selected from the group consisting of β-blockers, carbonic anhydrase inhibitors, $α_1$ antagonist, $α_2$ agonists, miotics, prostaglandin analogs, hypotensive lipids, and neutroprotectants.

9. The method of claim 5, wherein said agent is selected from the group consisting of timolol, betaxolol, levobetaxolol, carteolol, levobunolol, propranolol, brinzolamide, dorzolamide, nipradolol, lopidine, brimonidine, pilocarpine, epinephrine, latanoprost, travoprost, unoprostone, lumigan, eliprodil and R-eliprodil.

10. The composition of claim 3, further comprising one or more other agent for treating glaucoma wherein said the other agent is selected from the group consisting of β-blockers, carbonic anhydrase inhibitors, $α_1$ antagonists, $α_2$ agonists, miotics, prostaglandin analogs, hypotensive lipids, and neuroprotectants.

11. The composition of claim 10 wherein the other agent is selected from the group consisting of timolol, betaxolol, levobetaxolol, carteolol, levobunolol, propranolol brinzolamide, dorzolamide, nipradolol, iopidine, brimonidine, pilocarpine, epinephrine, latanoprost, travoprost, unoprostone, lumigan, eliprodil and R-eliprodil.

* * * * *